United States Patent [19]

Pastan et al.

[11] Patent Number: 4,806,494

[45] Date of Patent: Feb. 21, 1989

[54] MONOCLONAL ANTIBODY AGAINST OVARIAN CANCER CELLS (OVB-3)

[75] Inventors: Ira Pastan, Potomac; David J. Fitzgerald; Mark Willingham, both of Bethesda, all of Md.

[73] Assignee: The United States of America as represented by the Department of Health & Human Services, Washington, D.C.

[21] Appl. No.: 888,960

[22] Filed: Jul. 24, 1986

[51] Int. Cl.$^4$ .................. G01N 33/53; G01N 33/543; A61K 39/00; A61K 45/02
[52] U.S. Cl. .............................. 424/85.91; 436/518; 436/519; 436/548; 514/2; 530/387
[58] Field of Search ............. 436/548, 519, 119, 802, 436/823; 935/102, 103, 106, 07, 110; 435/68; 424/85, 88, 92; 514/2

[56] References Cited

U.S. PATENT DOCUMENTS

| | | | |
|---|---|---|---|
| 4,545,985 | 10/1985 | Paston et al. | 424/85 |
| 4,664,911 | 5/1987 | Uhr et al. | 424/88 |
| 4,666,845 | 5/1987 | Mattes et al. | 935/110 |
| 4,671,958 | 6/1987 | Rodwell et al. | 424/85 |
| 4,678,667 | 7/1987 | Meaves et al. | 424/85 |

OTHER PUBLICATIONS

Thorpe et al., "Monoclonal Antibody-Toxin Conjugates: Aiming the Magic Bullet", *Monoclonal Antibodies in Clinical Medicine*, McMichael et al., ed., Academic Press, London (1982), pp. 168–201.

*Primary Examiner*—Robert J. Warden
*Assistant Examiner*—Janelle Graeter
*Attorney, Agent, or Firm*—John S. Roberts, Jr.; Mishrilal L. Jain

[57] ABSTRACT

Monoclonal antibodies are produced which specifically bind to human ovarian cancer cells. These antibodies are conjugated to Pseudomonas exotoxin in order to produce an immunotoxin suitable for the chemotherapeutic treatment of human ovarian cancer.

5 Claims, No Drawings

MONOCLONAL ANTIBODY AGAINST OVARIAN CANCER CELLS (OVB-3)

BACKGROUND AND GENERAL DESCRIPTION OF THE INVENTION

Current approaches to cancer chemotherapy and other immunological therapies focus on the use of cell-specific therapeutic agents. Ideally, immunotoxins should discriminate to a high degree between target and non-target cells. The present invention discloses an immmunotoxin conjugate formed between monoclonal antibody OVB-3 (which specifically binds to human ovarian cancer cells) and Pseudomonas exotoxin.

Since the advent of the monoclonal antibody methodology disclosed in Koprowski et al (U.S. Pat. No. 4,172,124) many monoclonal antibodies designed to treat a wide variety of human ailments have been developed. However, two problems have prevented this methodolgy from being practiced more extensively. First, many monoclonal antibodies to hmman target (e.g. cancer) cells also bind to non-target (normal) human cells. Secondly, many of the toxin delivery systems reduce the effectiveness of the toxin, reduce the entry capacity of the toxin into the target cell, or are not specific enough to deliver a sufficent amount of toxin to the target site. The present invention discloses an immunotoxin which differentiates between normal and cancerous cells, is highly specific for human ovarian cancer cells, and is capable of carrying and delivering a toxin to the cancer cell without destroying the toxin's entry and lethal activity. In this manner, the present invention satisfies a long felt need in the area of cancer chemotherapy: very few ovarian cancer monoclonal antibodies exist, and those that do are not capable of delivering an exotoxin in condition for the cancer cell to internalize the endotoxin. Furthermore, the present invention uses recently developed technology to produce an effective immunotoxin which specifically binds to ovarian cancer cells without binding to normal human cells.

The present invention builds on the discovery disclosed by the same inventors in U.S. Pat. No. 4,545,985, titled "Pseudomonas Exotoxin Conjugate Immunotoxins." This patent is hereby incorporated by reference because it discloses the method used in the present invention for modifying Pseudomonas exotoxin so that the toxin will selectively kill target human tumor cells.

The present invention is an improvement on this process; with the production of highly specific monoclonal antibodies, human ovarian cancer may be targeted and treated by the products of this invention.

Pseudomonas exotoxin (PE) has been conjugated to a variety of monoclonal antibodies recognizing certain human tumors and to a monoclonal antibody recognizing the human y antigen blood group substance [Richert et al, *J. Biol. Chem.*, 258:8902–8907 (1983); and Fredman et al, J. Biol. Chem., 258:11206–11210 (1983)]. The toxin conjugates specifically kill the appropriate target cells. PE can now be conjugated to a variety of peptides, proteins, and growth factors that react with specific receptors on cells. These include sarcoma growth factors, melanocyte stimulating hormone (MSH) somatostatin, glucagon, insulin, transferrin, low density lipoprotein, calcitonin, alpha$_2$-macroglobulin, and lysine-bradykinin. Pseudomonas exotoxin is particularly preferable to other toxins (such as ricin or diphtheria toxin) because large amounts are easily prepared, because humans do not usually have neutralizing antibodies against it (as is the case with diphtheria toxin), and because it does not need to be separated into subunits before being conjugated (as does ricin toxin).

DEPOSIT STATEMENT

The subject matter of this invention, monoclonal antibody OVB-3 has been deposited in the American Type Culture Collection in Rockville, Md., under ATCC No. H89147, and will be maintained for a term of thirty (30) years or five (5) years after the last request for such deposit or for the effective life of the patent, whichever is longest. The deposit will be replaced if the culture mutates or becomes nonviable during the term of the deposit.

SPECIFIC DISCLOSURE

Pseudomonas exotxin (PE) is a known and readily available toxin isolated from *Pseudomonas aeruginosa*. The particular exotoxin used in this invention is commercially available through the Swiss Serum Company.

PE was chosen for this invention because it acts in the cytosol of the cell to inhibit protein synthesis by catalyzing the enzymatic (ADP-ribosylation) inactivation of Elongation Factor Two.

Monoclonal antibodies (Mabs) specific for ovarian cancer cells exist [see, for example, Bast et al, *J. Clin. Invest.*, 68:1331–1337 (1981); and Tsuji et al, *Cancer Research*, 45:2358–2362 (1985)], but either are poorly internalized by human ovarian cancer cells or do not exhibit the degree of specificity shown by the monoclonal antibody of the present invention.

Monoclonal antibody OVB-3 is produced by conventional methods. In general, mice are immunized with OVCAR-3, a human ovarian cancer cell line [described in Hamiliton et al, *Cancer Research*, 43:5379–5389 (1983)]. Spleen cells from the immunized mouse are then fused with a myeloma cell line, thus forming hybridomas which are capable of producing monoclonal antibodies which specifically bind to human ovarian cancer cells. One such Mab, OVB-3, is highly specific for human ovarian cancer, and is used to instruct the Pseudomonas exotoxin conjugate.

The Table shows the reactivity of monoclonal antibody OVB-3 with a variety of ovarian cancer cell lines and with normal human cells. This Table shows that the monoclonal antibody of this invention is highly specific for human ovarian cancer cells.

Pseudomonas exotoxin-monoclonal antibody OVB-3 conjugates (PE-OVB-3) are constructed either using a disulfide exchange reaction or by forming a thioether bond. Generally, PE is treated with 2-iminothiolane (formally, methyl-4-mercapto-butyrimidate) in order to introduce two thiol groups per molecule of toxin. This step is optimally conducted in 0.15 M KPO$_4$ (pH 8.0), 1 mM EGTA. Derivatized PE from the above step is then reacted with dithiobis(2-nitrobenzoic acid), DTNB. Purified OVB-3 is also treated with 2-iminothiolane in order to introduce one sulfhydryl group per molecule. The treated antibody is then mixed with excess treated PE at pH 8.0 and allowed to incubate for 2 hours at 23oC. At the end of the reaction, the pH is adjusted to 7.0 and cysteine is added to displace the TNB from any PE molecules that have not formed conjugates or that have one unreacted —SH group.

Alternatively, the antibody can be modified with m-maleimidobenzoyl N hydroxy-succinimide ester (MBS) and the resulting activated antibody is reacted with SH—PE—SH to produce a conjugate containing a thioether bond. This conjugate is more stable in an animal environment since it cannot be inactivated by reduction of the disulfide bond.

The resulting PE-OVB-3 conjugate is purified by gel filtration. Typically, 1-5 ml of conjugate at 3-5 mg/ml is passed over an HPLC gel filtration column, TSK-250 (600×21.5 mm). Aggregates in the void volume exhibit low activity and are discarded. Two conjugate peaks, of higher molecular weight than native antibody, are included in the column. These correspond to 2:1 and 1:1 antibody-toxin conjugates. Both peaks have high activity, but usually only the 1:1 conjugate is used for further studies. The conjugate is assayed by adding it to human ovarian cancer cells and measuring inhibition of protein synthesis or cell death. The ADP-ribosylating activity of the conjugates is also assayed in cell-free extracts, usually reticulocyte lysates, using $^{14}$C-NAD as described in Fitzgerald et al, *Cell,* 32:607 (1983). All experiments were conducted either in vivo in mice, or in vitro on human cells in tissue culture.

Approximately $50 \times 10^6$ ovarian cancer cells in 0.5 ml saline are injected intraperitoneally into nude mice. These cancer cells are allowed to establish for 4–5 days and then PE-OVB-3 is administered in 4 daily injections. Untreated mice die after 40 days with massive malignant ascites. PE-OVB-3 is cytotoxic for these ovarian cancer cells and kills a high enough percentage of them to allow the mice to live 40-50 days longer than mice receiving no treatment, mice receiving the antibody alone, or mice receiving an irrelevant antibody-PE conjugate. Furthermore, PE-OVB-3 is cytotoxic for cells expressing the OVB-3 receptor, but is inactive against receptornegative cells.

THE TABLE
Summary of Localization of OVB-3

| Tissue | Reactivity Detected | |
|---|---|---|
| Ovarian Tumors (NIH): | | |
| #1 (O.S.) | (++) | |
| #2 (G.) | (++) | |
| Ovarian Tumors (Alabama): | | repeat: |
| 86-M (poorly differentiated adenocarcinoma) | (++) | #2- (+++ var) |
| 86-R (mucinous well-differentiated adenocarcinoma) | (++) | #2- (++) |
| 81-N (mixed Mullerian poorly differentiated carcinoma) | (++) | #2- (++) |
| 86-O (serous cystadenocarcinoma) | (−) | #2- (+/−)-(+) |
| Breast Tumors (Cetus): | | |
| BCNA (invasive lobular or ductal carcinoma) | (+-++) | |
| BCBA (invasive ductal carcinoma) | (+-++) | |
| BCUA (Paget's disease of breast) | (−) | |
| BCTA (invasive scirrhous carcinoma) | (+/−) | |
| Pituitary | (−); occ. cells reactive in pars intermedia #2 repeat:(−); occ. cells in anterior lobe | |
| Thyroid | (++) epithelial follicular cells | |
| Parathyroid | (−) | |
| Breast | (++) ductal epithelium | |
| Heart | (−) | |
| Lung | (−); ?(+) peribronchiolar dendritic cells | |
| Liver | (−) | |
| Gallbladder | (−) | |
| Lymph Node | (++) scattered endothelial & germinal cells | |
| Spleen | (−) | |
| Bone Marrow | (−) | |
| Adrenal | (+) chromaffin cell granules?; (−) cortex | |
| Kidney | (++) apical surface of proximal tubule cells | |
| Prostate | (+++) secretion; (+/−) epithelial cells | |
| Testis | (−) seminiferous tubules | |
| Ovary | (−) | |
| Uterus | (−) | |

We claim:

1. Monoclonal antibody OVB-3 having all the characteristics of that antibody produced by the hydroma ell line which has been assigned ATCC Accession No. HB9147.

2. An immunotoxin conjugate for the chemotherapeutic alleviation of human ovarian cancer comprising a monoclonal antibody OVB-3 which specifically binds to ovarian cancer cells bonded to Pseudomonas exotoxin.

3. An immunotoxin conjugate comprising Pseudomonas exotoxin (PE) bound to a monoclonal antibody which specifically binds to ovarian cancer cells wherein said PE is modified by treatment with 2-iminothiolane followed by treatment with dithiobis(2-nitrobenzoic acid) and wherein said monoclonal antibody is modified by treatment with a reagent selected from the group consisting of 2-imminothiolane and m-maleimidobenzoyl N-hydroxysuccinimide ester under conditions which effect the formation of a disulfide or thioether bond between said PE and said monoclonal antibody.

4. A composition of matter comprising a monoclonal antibody of claim 1 conjugated with a *Pseudomonas exotoxin.*

5. A composition of matter comprising an monoclonal antibody of claim 1 in a carrier.

* * * * *